United States Patent
Putha et al.

(10) Patent No.: US 11,276,173 B1
(45) Date of Patent: Mar. 15, 2022

(54) PREDICTING LUNG CANCER RISK

(71) Applicant: Qure.ai Technologies Private Limited, Mumbai (IN)

(72) Inventors: Preetham Putha, Guntur (IN); Manoj Tadepalli, Gudivada (IN); Bhargava Reddy, Mumbai (IN); Tarun Raj, Vishakapatnam (IN); Ammar Jagirdar, Mumbai (IN); Pooja Rao, Pune (IN); Prashant Warier, Mumbai (IN)

(73) Assignee: QURE.AI TECHNOLOGIES PRIVATE LIMITED, Mumbai (IN)

( * ) Notice: Subject to any disclaimer, the term of this patent is extended or adjusted under 35 U.S.C. 154(b) by 0 days.

(21) Appl. No.: 17/383,845

(22) Filed: Jul. 23, 2021

(30) Foreign Application Priority Data

May 24, 2021 (IN) .............................. 202121023188

(51) Int. Cl.
*G06T 7/00* (2017.01)
*A61B 6/00* (2006.01)
(Continued)

(52) U.S. Cl.
CPC .............. *G06T 7/0014* (2013.01); *A61B 6/50* (2013.01); *G06N 3/08* (2013.01); *G06T 7/11* (2017.01);
(Continued)

(58) Field of Classification Search
CPC .................... G06T 7/0014; G06T 7/11; G06T 2207/20081; G06T 2207/30064;
(Continued)

(56) References Cited

U.S. PATENT DOCUMENTS 6,738,499 B1 * 5/2004 Doi ....................... G06T 7/0012
382/128
10,553,311 B2 * 2/2020 Lyman ................... A61B 6/503
(Continued)

FOREIGN PATENT DOCUMENTS

CN 107103187 B 12/2020
WO 2021015913 A1 1/2021

OTHER PUBLICATIONS

Duan et al., "Development of a machine learning-based multimode diagnosis system for lung cancer", Aging, vol. 12, No. 10, 2020, pp. 9840-9854 (Year: 2020).*
(Continued)

*Primary Examiner* — Nay A Maung
*Assistant Examiner* — Jose M Torres
(74) *Attorney, Agent, or Firm* — Shumaker, Loop & Kendrick, LLP (57) ABSTRACT

A system and method for predicting a lung cancer risk based on a chest X-ray in which a nodule is detected in a chest of a patient based on an analysis of the chest X-ray using an image processing technique. A region of interest associated with the nodule is identified using the image processing technique. The region of interest is further analyzed using deep learning to determine a plurality of characteristics associated with the nodule. The plurality of characteristics comprises a size of the nodule, a calcification in the nodule, a homogeneity of the nodule and a spiculation of the nodule. Further, the plurality of characteristics is compared with a trained data model using deep learning. Based on the comparison, a risk score associated with the nodule is generated. Further, the lung cancer risk is predicted when the risk score exceeds a predefined threshold value.

15 Claims, 6 Drawing Sheets

(51) Int. Cl.

| | |
|---|---|
| *G16H 30/20* | (2018.01) |
| *G16H 30/40* | (2018.01) |
| *G16H 50/20* | (2018.01) |
| *G16H 50/30* | (2018.01) |
| *G06N 3/08* | (2006.01) |
| *G06T 7/11* | (2017.01) |
| *G16H 50/70* | (2018.01) |
| *G16H 10/60* | (2018.01) |
| *G16H 70/60* | (2018.01) |

(52) U.S. Cl.
CPC ............. *G16H 30/20* (2018.01); *G16H 30/40* (2018.01); *G16H 50/20* (2018.01); *G16H 50/30* (2018.01); *G16H 50/70* (2018.01); *G06T 2207/10116* (2013.01); *G06T 2207/20081* (2013.01); *G06T 2207/30064* (2013.01); *G16H 10/60* (2018.01); *G16H 70/60* (2018.01)

(58) Field of Classification Search
CPC . A61B 6/50; G06N 3/08; G16H 10/60; G16H 30/20; G16H 30/40; G16H 50/20; G16H 50/30; G16H 50/70; G16H 70/60
See application file for complete search history.

(56) References Cited

U.S. PATENT DOCUMENTS

| | | | |
|---|---|---|---|
| 2004/0252870 A1* | 12/2004 | Reeves | G06T 7/0012 382/128 |
| 2005/0207630 A1* | 9/2005 | Chan | A61B 6/583 382/131 |
| 2007/0019852 A1* | 1/2007 | Schildkraut | G06T 7/0012 382/132 |
| 2008/0205717 A1* | 8/2008 | Reeves | G06T 5/002 382/128 |
| 2016/0260211 A1* | 9/2016 | Gillies | G16H 50/30 |
| 2018/0068083 A1* | 3/2018 | Cohen | G16B 40/20 |
| 2018/0341748 A1 | 11/2018 | Lyman et al. | |
| 2019/0131016 A1 | 5/2019 | Cohen et al. | |
| 2020/0160997 A1* | 5/2020 | Bagci | G16H 70/60 |
| 2021/0233241 A1* | 7/2021 | Washko, Jr. | G06K 9/46 |

OTHER PUBLICATIONS

Ciompi et al., "Towards automatic pulmonary nodule management in lung cancer screening with deep learning", Scientific Reports, 2017; 7: 46479, pp. 1-10 (Year: 2017).*

* cited by examiner

PREDICTING LUNG CANCER RISK

PRIORITY INFORMATION

The present application claims priority from the Indian patent application numbered 202121023188 filed on May 24, 2021 in India.

TECHNICAL FIELD

The present subject matter described herein, in general, relates to a system and a method for predicting a lung cancer risk. More particularly, to predicting the lung cancer risk based on a chest X-ray.

BACKGROUND

Techniques such as a Computed Topography (CT) scan and an X-ray imaging are known well and widely in a medical field. These techniques are primarily used for a diagnosis of an abnormality in a body part of a patient. It is to be noted that the CT scan provides an accurate diagnosis compared to the X-ray imaging. Typically, doctors also prefer the CT scan for a confirmation of any abnormality. As a general practice, whenever any abnormality is detected in the X-ray imaging of the patient, the doctors suggest the patient to go through few CT scans. However, it is to be noted that high intensity radiations are used in the CT scan. Hence, the CT scan radiations may be dangerous for the patient's health. Also, the CT scan is a costly technique. In addition, once the CT scan is received, the doctors analyze the CT scan manually, and advise the patient accordingly. It is to be noted that the manual analysis of the CT scan is a time-consuming task.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for predicting a lung cancer risk based on a chest X-ray. This summary is not intended to identify essential features of the claimed subject matter nor is it intended for use in determining or limiting the scope of the claimed subject matter.

In one implementation, a method for predicting a lung cancer risk based on a chest X-ray is disclosed. Initially, a chest X-ray of a patient may be received. Further, a nodule may be detected in the chest X-ray. In one aspect, the nodule may be detected using an image processing technique. The nodule may be an opacity present in a chest. Furthermore, a region of interest associated with the nodule may be identified using the image processing technique. The region of interest may be an area surrounding the nodule. Upon identification of the region of interest, a plurality of characteristics associated with the nodule may be determined based on an analysis of the region of interest. In one aspect, the plurality of characteristics may be determined using deep learning. The plurality of characteristics may comprise a size of the nodule, a calcification in the nodule, a homogeneity of the nodule and a speculation of the nodule. Further, the plurality of characteristics may be compared with a trained data model using deep learning. In one aspect, the trained data model may comprise historical data related to different sizes of nodules, concentration of calcification in nodules, information associated with homogeneity of nodules, and spiculations for the different nodules. Furthermore, a risk score for the nodule may be generated in real time based on the comparison of the plurality of characteristics with the trained data model. Finally, a lung cancer risk may be predicted when the risk score for the nodule exceeds a predefined threshold value. In one aspect, the aforementioned method for predicting a lung cancer risk based on a chest X-ray may be performed by a processor using programmed instructions stored in a memory.

In another implementation, a non-transitory computer readable medium embodying a program executable in a computing device for predicting a lung cancer risk based on a chest X-ray is disclosed. The program may comprise a program code for receiving a chest X-ray of a patient. Further, the program may comprise a program code for detecting a nodule in the chest X-ray. In one aspect, the nodule may be detected using an image processing technique. The nodule may be an opacity present in a chest. Furthermore, the program may comprise a program code for identifying a region of interest associated with the nodule using the image processing technique. In one aspect, the region of interest may be an area surrounding the nodule. The program may comprise a program code for determining a plurality of characteristics associated with the nodule based on an analysis of the region of interest. In one aspect, the plurality of characteristics may be determined using deep learning. The plurality of characteristics may comprise a size of the nodule, a calcification in the nodule, a homogeneity of the nodule and a spiculation of the nodule. Further, the program may comprise a program code for comparing the plurality of characteristics with a trained data model using deep learning. In one aspect, the trained data model may comprise historical data related to different sizes of nodules, concentration of calcification in nodules, information associated with homogeneity of nodules, and spiculations for the different nodules. Furthermore, the program may comprise a program code for generating a risk score for the nodule in real time based on the comparison of the plurality of characteristics with the trained data model. Finally, the program may comprise a program code for predicting a lung cancer risk when the risk score for the nodule exceeds a predefined threshold value.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for predicting a lung cancer risk based on a chest X-ray disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving", "detecting," "identifying," "determining," "comparing," "generating," "predicting," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for predicting a lung cancer risk based on a chest X-Ray. Typically, a medical professional recommends performing a CT scan of the chest to ascertain the lung cancer risk. It is important to note that the CT scan exposes the patient to harmful radiations which are dangerous for the body. In addition, the CT scans are costly as compared to the chest X-ray. More importantly, the present invention discloses a cost effective and an automatic process for analyzing the chest X ray to determine the lung cancer risk. Initially, the chest X-ray of a patient is analyzed to detect a nodule in the chest X-ray. Further, the nodule may be analyzed to determine a plurality of characteristics associated with the nodule. It may be noted that the plurality of characteristics may be determined using deep learning. Furthermore, the plurality of characteristics may be analyzed to predict the lung cancer risk.

While aspects of described system and method predicting a lung cancer risk based on a chest X-ray may be implemented in any number of different computing systems, environments, and/or configurations, the embodiments are described in the context of the following exemplary system.

Figure 1:
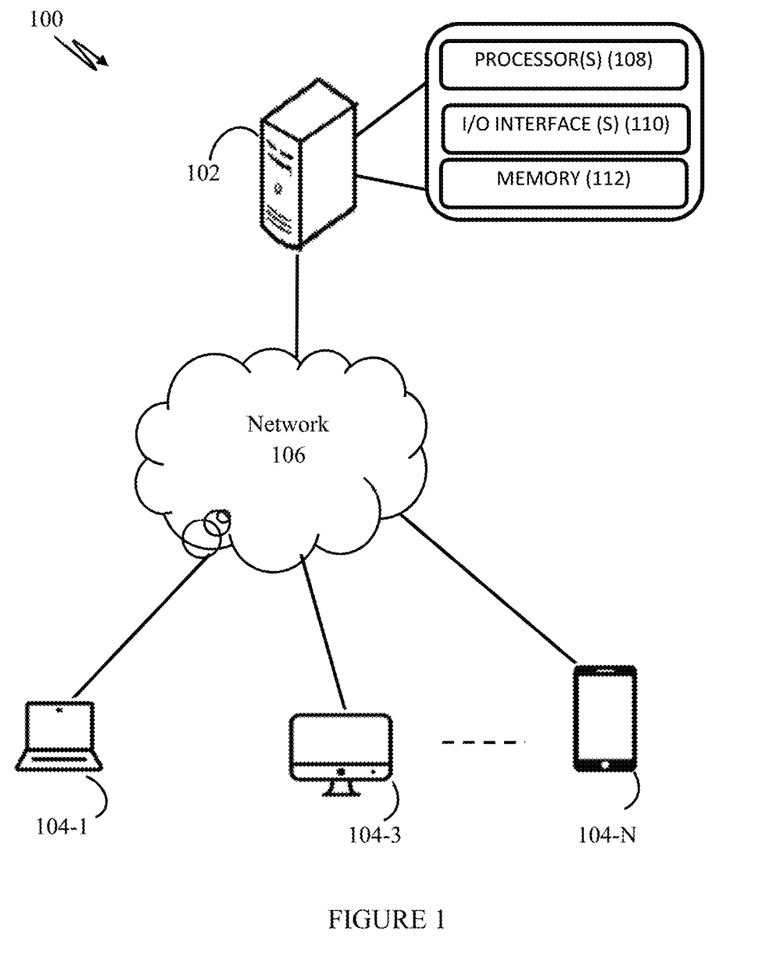
FIG. 1 illustrates a network implementation of a system for predicting a lung cancer risk based on a chest X-ray, in accordance with an embodiment of the present subject matter.

Referring now to FIG. 1, a network implementation 100 of a system 102 for predicting a lung cancer risk based on a chest X-ray is disclosed. It may be noted that one or more users may access the system 102 through one or more user devices 104-1, 104-3 . . . 104-N, collectively referred to as user devices 104, hereinafter, or applications residing on the user devices 104. In one aspect, the one or more users may comprise a doctor, a lab assistance and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-3 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for predicting a lung cancer risk based on a chest X-ray. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for predicting a lung cancer risk based on a chest X-ray. The system 102 may predict the lung cancer risk in real time without any human intervention. The lung cancer risk may be predicted automatically using deep learning. In order to predict the lung cancer risk, initially, the system 102 may receive the chest X-ray of a patient. In one aspect, the chest X-ray may produce images of heart, lungs, airways, blood vessels and the bones of the spine and the chest.

Further, the system 102 may analyze the chest X-ray using an image processing technique. Based on the analysis, the system 102 may detect an information corresponding to the lung's parameters including an opacity, a consolidation, a fibrosis, a nodule, a emphysema and a cavity, pleura including a blunted costophrenic angle, pleural effusion and pneumothorax, mediastinum including tracheal shift and hilar prominence, a cardiomegaly corresponding to the heart, a diaphragm including raised or tented diaphragm and pneumoperitoneum, placement of tubes including a gastric tube, and bones including scoliosis and rib fracture.

In an embodiment, the system 102 may detect the nodule in the chest X-ray using the image processing technique. The nodule may be an opacity or a node present in a chest of the patient. In an example, multiple nodules may be detected in the chest X-ray of the patient. Upon detecting the nodule, the system 102 may identify a region of interest in the chest X-ray. The region of interest may be associated with the nodule. The region of interest may be identified using the image processing technique. In an aspect, the region of interest may be an area surrounding the nodule. In an example, the region of interest may comprise one or more nodules.

Further to identifying the region of interest, the system 102 may determine a plurality of characteristics associated with the nodule. The plurality of characteristics may be determined by analyzing the region of interest using deep learning. The plurality of characteristics may comprise a size of the nodule, a calcification in the nodule, a homogeneity of the nodule and a spiculation of the nodule. In one embodiment, deep learning (may also be called as deep learning techniques) may be a part of a machine learning family. The deep learning techniques may comprise multiple layers in a network. The deep learning techniques may comprise a Convolutional Neural Network (CNN) technique. The deep learning techniques may use a trained data model for an operation. The trained data model comprises historical information, chest X-rays of a set of patients, medical history of the set of patients, the information associated to the nodules for the set of patients. It may be noted that the trained data model may be trained using a continuous learning approach like Reinforcement Learning techniques. The trained data model may correspond to data learned by the system to operate efficiently. The trained data model may enable an accurate operation of the deep learning techniques. In one aspect, the system 102 may use the deep learning techniques to determine the plurality of characteristics as shown in FIG. 2.

Figure 2:
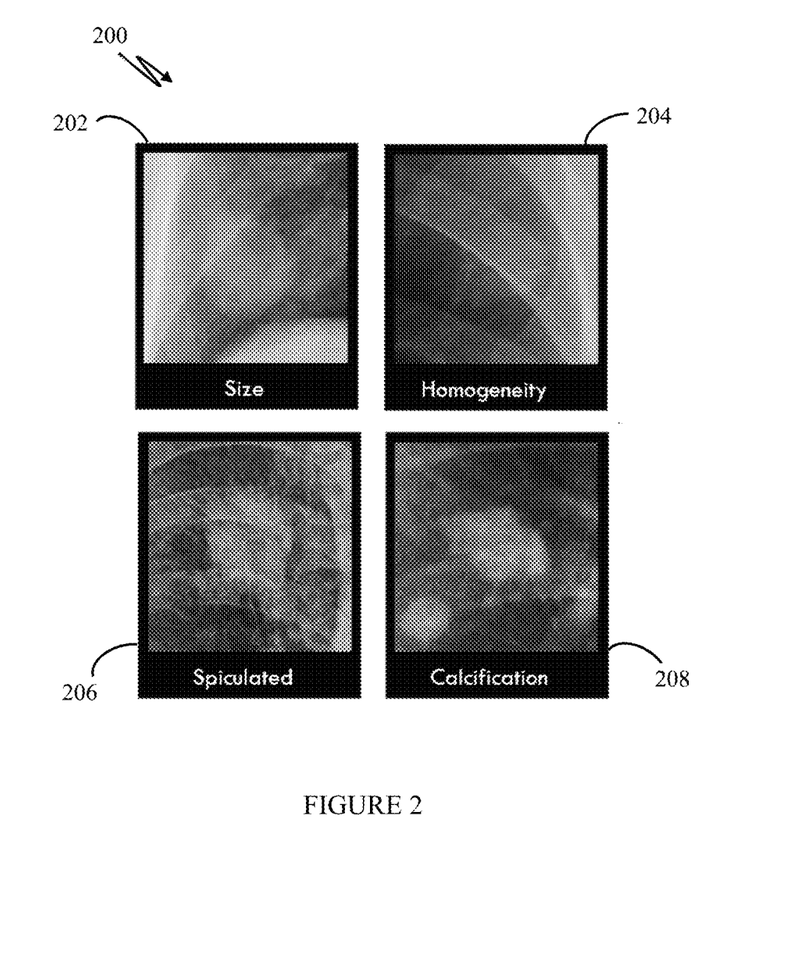
FIG. 2 illustrates a chest X-ray of a patient, in accordance with an embodiment of the present subject matter.

Referring now to FIG. 2, a chest X-ray (200) of a patient is shown in accordance with an embodiment of the present subject matter. In one embodiment, the chest X-ray may show a plurality of characteristics comprising a size 202 of the nodule, a calcification 208 in the nodule, a homogeneity 204 of the nodule and a spiculation 206 of the nodule.

In one aspect, the size 202 of the nodule may be 2 mm, 10 mm, 7 mm and the like. Further, the calcification 208 in the nodule may indicate an amount of calcium present in the nodule. In one example, if the amount of calcium exceeds a predefined amount of calcium, then the nodule may be referred as a calcified nodule. Furthermore, the homogeneity 204 of the nodule may indicate a texture of the nodule. The spiculation 206 of the nodule may indicate a border of the nodule. In one embodiment, the system 102 may detect multiple nodules in the chest X-ray. In the embodiment, a count of nodules may also be determined. The count of nodules corresponds to a number of nodules detected in the chest X-ray.

Referring again to FIG. 1, the system 102 may compare the plurality of characteristics with the trained data model. The plurality of characteristics and the trained data model may be compared using the Convolutional Neural Network (CNN) technique. In one embodiment, the trained data model may comprise historical data related to different sizes of nodules, concentration of calcification in nodules, information associated with homogeneity of nodules, and spiculations for the different nodules. In one aspect, the trained data model may be generated based on continuously learning data associated with a set of patients using deep learning. The trained data model may enable an accurate analysis.

In one aspect, the historical data may comprise historical clinical reports and historical chest X-rays associated with the set of patients. In an example, the set of patients may comprise patients suffering from a lung cancer. In another aspect, the historical data may comprise a previous clinical report and a previous chest X-ray of the patient.

In one exemplary embodiment, the Convolutional Neural Network (CNN) technique may be a part of the deep learning. Further, the CNN technique may comprise an input layer, an output layer, and multiple hidden layers. It may be understood that, the hidden layers may comprise convolutional layers, pooling layers, fully connected layers, and normalization layers. It may be noted that the convolutional layers may apply a convolution operation to the input, passing the result to the next layer. The local or global pooling layers may combine the outputs of neuron clusters at one layer into a single neuron in the next layer. The fully connected layers may connect every neuron in one layer to every neuron in another layer. An advantage of the CNN technique may be that the CNN network may learn the filters that may require to behand-engineered in the traditional algorithms. In one aspect, the system 102 may use the CNN technique to compare the plurality of characteristics with the trained data model.

In one embodiment, the system 102 may compare the size 202 of the nodule with the different sizes of nodules. Further, the system 102 may compare the calcification 208 in the nodule with the different concentration of calcification in nodules. Furthermore, the system 102 may compare the homogeneity 204 of the nodule with the information associated with homogeneity of nodules. The system 102 may further compare the spiculation 206 of the nodule with the spiculations for the different nodules. It may be noted that the comparison may be a one-to-one comparison of each characteristic from the plurality of characteristics with the trained data model using the CNN technique.

Subsequently, the system 102 may generate a risk score associated with the nodule. The risk score may be generated in real time. In one embodiment, the system 102 may compare the plurality of characteristics with the trained data model. Based on the comparison, a score for each characteristic may be determined. Further, a weightage may be predefined for each characteristic. In one example, the score associated with each characteristic and the weightage may be used to generate the risk score. In one aspect, the risk score may be generated using the deep learning techniques.

Upon generating the risk score, the system 102 may predict the lung cancer risk. The lung cancer risk may be predicted based on a comparison of the risk score with a predefined threshold value. The lung cancer risk may be categorized as a low risk, a high risk and a moderate risk. In one embodiment, if the risk score exceeds the predefined threshold value, the lung cancer risk may be the high risk. The high risk may indicate that the nodule is cancerous. In another embodiment, if the risk score is less than the predefined threshold value, the lung cancer risk may be the low risk. In yet another embodiment, if the risk score is equal to the predefined threshold value, the lung cancer risk may be the moderate risk.

In one embodiment, the system 102 may predict a type of the nodule. The type of the nodule may be a cancerous nodule or a noncancerous nodule. In one example, the noncancerous nodule may be a calcified granuloma. The cancerous nodule may be a neoplastic lesion.

In one aspect, the system 102 may monitor a change in the size of the nodule over a period. The change in the size of the nodule may be monitored based on the previous chest X-ray of the patient. The change in the size of the nodule may be an increase in size or a decrease in size. The increase in size may indicate the high risk of a lung cancer. The decrease in size may indicate the low risk of the lung cancer. In one embodiment, an amount of the change in the size of the nodule may indicate the lung cancer risk.

In one example, the size of the nodule in the previous chest X-ray of the patient may be 4 mm. Further, the size of the nodule in the chest X-ray may be 8 mm. It may indicate that the size of the nodule is increased and hence the high risk of the lung cancer. In another example, the size of the nodule in the previous chest X-ray of the patient may be 4 mm. Further, the size of the nodule in the chest X-ray May be 2 mm. It may indicate that the size of the nodule is decreased and hence the low risk of the lung cancer.

Figure 3:
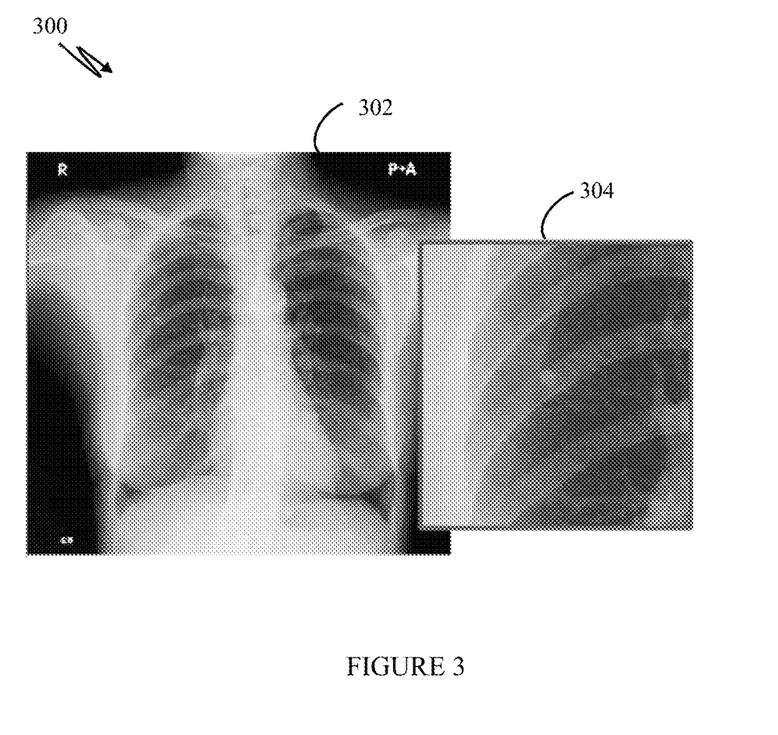
FIG. 3 and FIG. 4 illustrate exemplary embodiments of the system for predicting the lung cancer risk, in accordance with an embodiment of the present subject matter.
Figure 4:
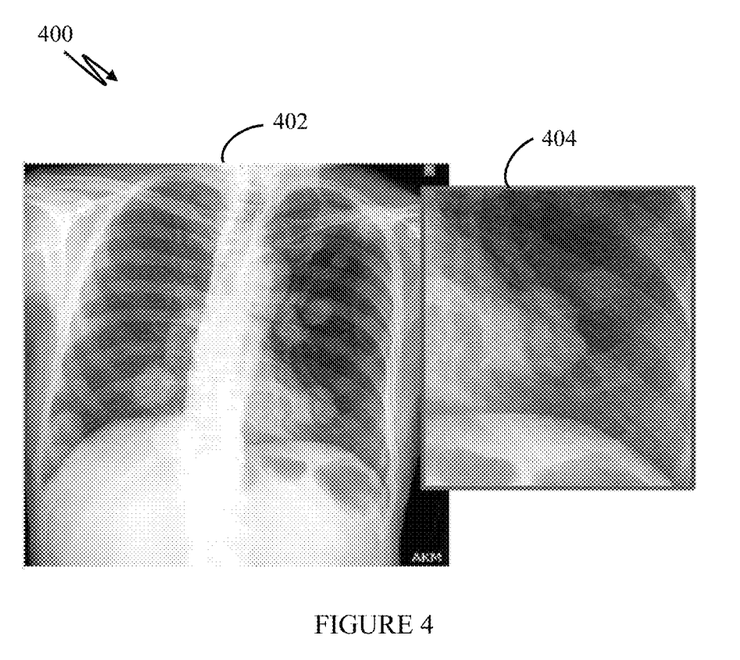

Referring now to FIG. 3 and FIG. 4, exemplary embodiments of the system for predicting the lung cancer risk is disclosed, in accordance with an embodiment of the present subject matter. In one embodiment, the FIG. 3 may show a low risk scenario (300) of the lung cancer risk. In one embodiment, the FIG. 4 may show a high risk scenario (400) of the lung cancer risk.

Referring to the FIG. 3, a chest X-ray 302 and a region of interest 304 may be shown. In an embodiment, construe detection of a nodule in the chest X-ray 302 of a patient. Further, a size of the nodule may be 8 mm, a calcification in the nodule may be determined as YES i.e., the calcium is present in the nodule, a homogeneity of the nodule may be determined as YES, and a spiculation of the nodule may be determined as NO.

In one aspect, the size of the nodule may be compared with different sizes of the nodules present in a trained data model. The different sizes of the nodules may be 2.5 mm, 3 mm, 5 mm, 7 mm, 10 mm and the like. In one example, the size of the nodule may vary from 0.2 mm to 10 mm. Upon comparing, it may be noted that the size of the nodule is less than a threshold size. In one aspect, the threshold size stored in the trained data model may be 10 mm. Similarly, the calcification in the nodule may be compared with different concentration of calcification in nodules. The homogeneity of the nodule may be compared with information associated with homogeneity of nodules. The spiculation of the nodule may be compared with spiculations for the different nodules.

Subsequently, a score for each characteristic may be determined based on the comparison. In an example, the score for the size of the nodule may be 2, the score for the calcification in the nodule may be 6, the score for the homogeneity of the nodule as 0, the score for the spiculation of the nodule as 1. Further, a weightage of each characteristic may be 2.5. Furthermore, the score for each characteristic and the weightage may be used to determine a risk score. The risk sore may be determined as 5.6. The risk score may be further compared with a predefined threshold value. In one embodiment, the predefined threshold value may be 8. It may be noted that the risk score is less than the predefined threshold value. Thus, the lung cancer risk may be predicted to be a low risk. In an example, the nodule may be referred as a calcified granuloma.

Referring to the FIG. 4, a chest X-ray 402 and a region of interest 404 may be shown. In an embodiment, construe detection of a nodule in the chest X-ray 402 of a patient. Further, a size of the nodule may be 12 mm, the calcification in the nodule may be determined as NO i.e., the calcium is not present in the nodule, the homogeneity of the nodule may be determined as YES, and the spiculation of the nodule may be determined as YES.

In one aspect, the size of the nodule may be compared with different sizes of the nodules present in a trained data model. The different sizes of the nodules may be 2.5 mm, 3 mm, 5 mm, 7 mm, 10 mm and the like. Upon comparing, it may be noted that the size of the nodule exceeds a threshold size. In one aspect, the threshold size stored in the trained data model may be 10 mm. Similarly, the calcification in the nodule may be compared with different concentration of calcification in nodules. The homogeneity of the nodule may be compared with information associated with homogeneity of nodules. The spiculation of the nodule may be compared with spiculations for the different nodules.

Subsequently, a score for each characteristic may be determined based on the comparison. In an example, the score for the size of the nodule may be 9, the score for the calcification in the nodule may be 0, the score for the homogeneity of the nodule as 1, the score for the spiculation of the nodule as 5. Further, a weightage of each characteristic may be 2.5. Furthermore, the score of each characteristic and the weightage may be used to compute a risk score. The risk score may be computed as 9.3. In one embodiment, the predefined threshold value may be 8. It may be noted that the risk score exceeds the predefined threshold value. Thus, the lung cancer risk may be predicted to be a high risk. In an example, the nodule may be refereed as a neoplastic lesion. It may indicate that the nodule is abnormal and contains cancerous cells.

Figure 5:
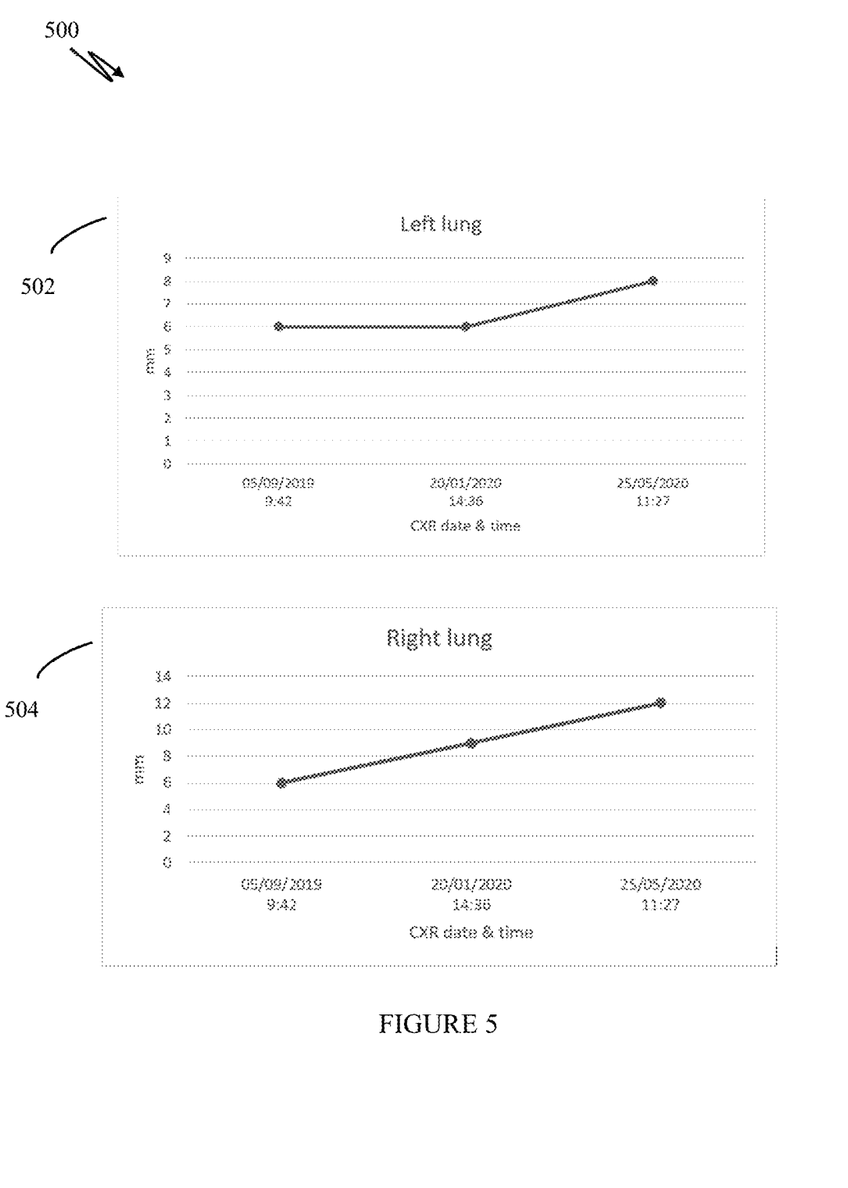
FIG. 5 illustrates an exemplary embodiment of the system for monitoring a change in size of a nodule, in accordance with an embodiment of the present subject matter.

Referring now to FIG. 5, an exemplary embodiment (500) of a system for monitoring a change in size of a nodule, is illustrated in an accordance with the present subject matter. In order to illustrate further, construe a graphical representation of a size of nodule Vs. a date and time of a chest X-ray. Two nodules may be detected in the chest X-ray of a patient. One nodule may be present in a left lung and referred as a left nodule. Another node may be present in a right lung and may be referred as a right nodule. In one embodiment, the graphical representation 502 may correspond to the left nodule and the graphical representation 504 may correspond to the right nodule.

In one example, a first chest X-ray is received on date Sep. 5, 2019 at time 9:42, a second chest X-ray is received on date Jan. 20, 2020 at time 14:36 and a third X-ray is received on date May 25, 2020 at time 11:27. In the first chest X-ray, a size of the left nodule is 6 mm and a size of the right nodule is 6 mm In the second chest X-ray, the size of the left nodule is 6 mm and the size of the right nodule is 9 mm In the third chest X-ray, the size of the left nodule is 8 mm and the size of the right nodule is 12 mm.

Further, the first chest X-ray, the second chest X-ray and the third chest X-ray may be analyzed to monitor the change in size. It may be noted that the size of the left nodule is increased by 2 mm and the size of the right nodule is increased by 6 mm. Thus, the change in size of the left nodule is less and the change in size of the right nodule is more. It may be noted that the change in size of the right nodule indicates a high risk of a lung cancer.

Figure 6:
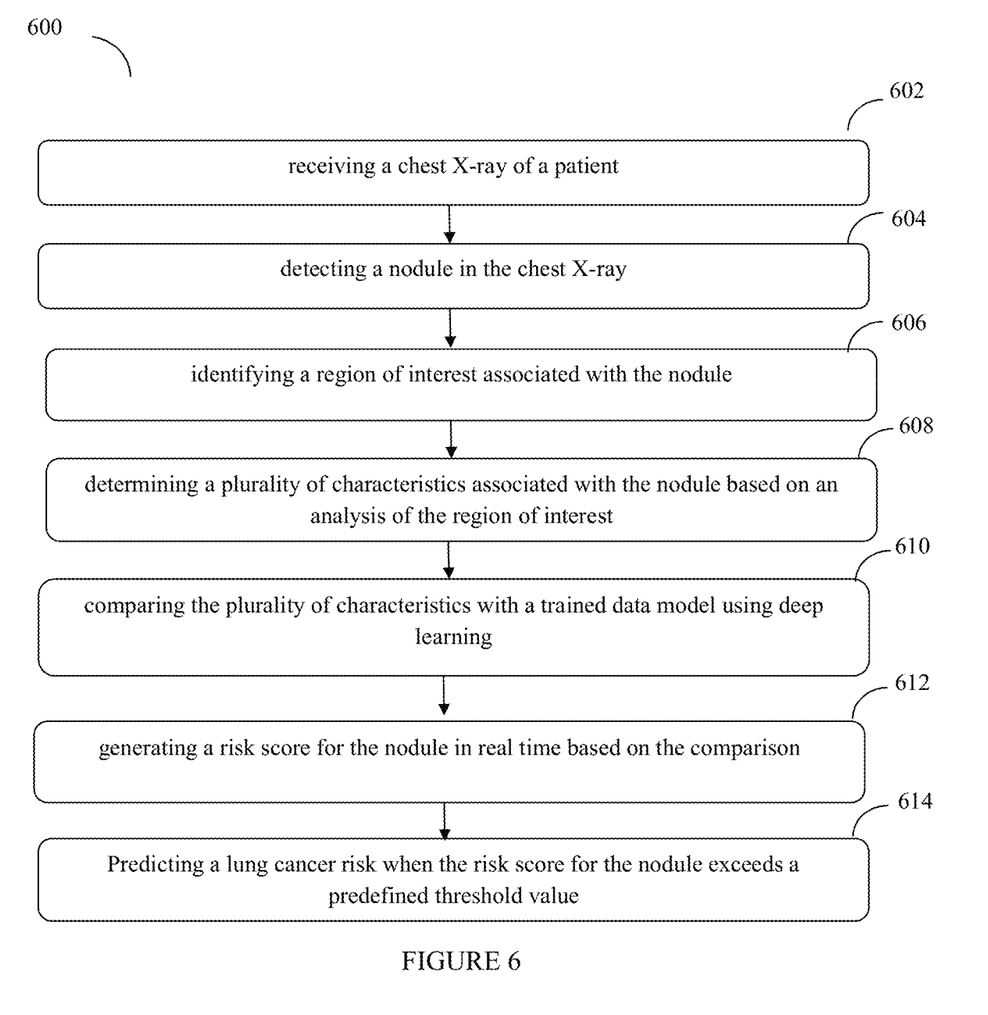
FIG. 6 illustrates a method for predicting a lung cancer risk based on a chest X-ray, in accordance with an embodiment of the present subject matter.

Referring now to FIG. 6, a method 600 for predicting a lung cancer risk based on a chest X-ray is shown, in accordance with an embodiment of the present subject matter. The method 600 may be described in the general context of computer executable instructions. Generally, computer executable instructions can include routines, programs, objects, components, data structures, procedures, modules, functions, etc., that perform particular functions or implement particular abstract data types.

The order in which the method 600 is described is not intended to be construed as a limitation, and any number of the described method blocks can be combined in any order to implement the method 600 or alternate methods for predicting a lung cancer risk based on a chest X-ray. Additionally, individual blocks may be deleted from the method 600 without departing from the spirit and scope of the subject matter described herein. Furthermore, the method 600 for predicting a lung cancer risk based on a chest X-ray can be implemented in any suitable hardware, software, firmware, or combination thereof. However, for ease of explanation, in the embodiments described below, the method 600 may be considered to be implemented in the above described system 102.

At block 602, a chest X-ray of a patient may be received.

At block 604, a nodule may be detected in the chest X-ray. In an aspect, the nodule may be detected using an image processing technique. The nodule may be an opacity present in a chest.

At block 606, a region of interest associated with the nodule may be identified. In one aspect, the region of interest may be identified using the image processing technique. The region of interest may be an area surrounding the nodule.

At block 608, a plurality of characteristics associated with the nodule may be determined. In one aspect, the plurality of characteristics may be determined based on an analysis of the region of interest. The plurality of characteristics may be determined using deep learning. The plurality of characteristics may comprise a size of the nodule, a calcification in the nodule, a homogeneity of the nodule and a spiculation of the nodule.

At block 610, the plurality of characteristics may be compared with a trained data model using deep learning. In one aspect, the trained data model may comprise historical data related to different sizes of nodules, concentration of calcification in nodules, information associated with homogeneity of nodules, and spiculations for the different nodules.

At block 612, a risk score for the nodule may be generated in real time. In one aspect, the risk score may be generated based on the comparison of the plurality of characteristics with the trained data model.

At block 614, a lung cancer risk may be predicted. In one aspect, the lung cancer risk may be predicted when the risk score for the nodule exceeds a predefined threshold value.

Exemplary embodiments discussed above may provide certain advantages. Though not required to practice aspects of the disclosure, these advantages may include those provided by the following features.

Some embodiments of the system and the method enable predicting a lung cancer risk automatically using deep learning techniques.

Some embodiments of the system and the method enable predicting the lung cancer risk in real time without any human intervention.

Some embodiments of the system and the method enable predicting the lung cancer risk accurately based on a chest X-ray.

Some embodiments of the system and the method enable determining multiple parameters from the chest X-ray using the deep learning techniques.

Some embodiments of the system and the method enable monitoring a change in size of a nodule detected in the chest X-ray.

Some embodiments of the system and the method provide a cost effective method for determining the lung cancer risk in real time.

Although implementations for methods and system for predicting a lung cancer risk based on a chest X-ray have been described in language specific to structural features and/or methods, it is to be understood that the appended claims are not necessarily limited to the specific features or methods described. Rather, the specific features and methods are disclosed as examples of implementations for predicting a lung cancer risk based on a chest X-ray.

We claim:

1. A method for predicting a lung cancer risk based on a chest X-ray, the method comprising:
   receiving, by a processor, a chest X-ray of a patient;
   detecting, by the processor, a nodule in the chest X-ray, wherein the nodule is detected using an image processing technique, and wherein the nodule is an opacity present in a chest;
   identifying, by the processor, a region of interest associated with the nodule using the image processing technique, wherein the region of interest is an area surrounding the nodule;

determining, by the processor, a plurality of characteristics associated with the nodule based on an analysis of the region of interest, wherein the plurality of characteristics is determined using deep learning, and wherein the plurality of characteristics comprises a size of the nodule, a calcification in the nodule, a homogeneity of the nodule and a spiculation of the nodule;

comparing, by the processor, the plurality of characteristics with a trained data model using deep learning, wherein the trained data model comprises historical data related to different sizes of nodules, concentration of calcification in nodules, information associated with homogeneity of nodules, and spiculations for the different nodules;

generating, by the processor, a risk score for the nodule in real time based on the comparison of the plurality of characteristics with the trained data model; and predicting, by the processor, a lung cancer risk when the risk score for the nodule exceeds a predefined threshold value.

2. The method as claimed in claim 1, further comprises monitoring a change in size of the nodule based on a previous chest X-ray corresponding to the patient.

3. The method as claimed in claim 2, wherein the change in size is one of an increase in size or a decrease in size, wherein the increase in size indicates a high risk of a lung cancer, and wherein the decrease in size indicates a low risk of the lung cancer.

4. The method as claimed in claim 1, wherein the historical data corresponds to historical clinical reports and historical chest X-rays of a set of patients.

5. The method as claimed in claim 1, wherein the calcification in the nodule indicates an amount of calcium deposits in the nodule, the homogeneity of the nodule indicates a texture of the nodule, and the spiculation of the nodule indicates a border of the nodule.

6. The method as claimed in claim 1, wherein the trained data model is generated based on continuously learning data associated with a set of patients using the deep learning technique.

7. The method as claimed in claim 1, wherein the size of the nodule varies from 0.2 mm to 10 mm.

8. A system for predicting a lung cancer risk based on a chest X-ray, the system comprising:
a memory;
a processor coupled to the memory, wherein the processor is configured to execute a set of instructions stored in the memory to:
receive a chest X-ray of a patient;
detect a nodule in the chest X-ray, wherein the nodule is detected using an image processing technique, and wherein the nodule is an opacity present in a chest;
identify a region of interest associated with the nodule using the image processing technique, wherein the region of interest is an area surrounding the nodule;
determine a plurality of characteristics associated with the nodule based on an analysis of the region of interest, wherein the plurality of characteristics is determined using deep learning, and wherein the plurality of characteristics comprises a size of the nodule, a calcification in the nodule, a homogeneity of the nodule and a spiculation of the nodule;
compare the plurality of characteristics with a trained data model using deep learning, wherein the trained data model comprises historical data related to different sizes of nodules, concentration of calcification in nodules, information associated with homogeneity of nodules, and spiculations for the different nodules;
generate a risk score for the nodule in real time based on the comparison of the plurality of characteristics with the trained data model; and
predict a lung cancer risk when the risk score for the nodule exceeds a predefined threshold value.

9. The system as claimed in claim 8, further configured to monitor a change in size of the nodule based on a previous chest X-ray corresponding to the patient.

10. The system as claimed in claim 9, wherein the change in size is one of an increase in size or a decrease in size, wherein the increase in size indicates a high risk of a lung cancer, and wherein the decrease in size indicates a low risk of the lung cancer.

11. The system as claimed in claim 8, wherein the historical data corresponds to historical clinical reports and historical chest X-rays of a set of patients.

12. The system as claimed in claim 8, wherein the calcification in the nodule indicates an amount of calcium deposits in the nodule, the homogeneity of the nodule indicates a texture of the nodule, and the spiculation of the nodule indicates a border of the nodule.

13. The system as claimed in claim 8, wherein the trained data model is generated based on continuously learning data associated with a set of patients using the deep learning technique.

14. The system as claimed in claim 8, wherein the size of the nodule varies from 0.2 mm to 10 mm.

15. A non-transitory computer program product having embodied thereon a computer program for predicting a lung cancer risk based on a chest X-ray, the computer program product storing instructions, the instructions comprising instructions for:
receiving a chest X-ray of a patient;
detecting a nodule in the chest X-ray, wherein the nodule is detected using an image processing technique, and wherein the nodule is an opacity present in a chest;
identifying a region of interest associated with the nodule using the image processing technique, wherein the region of interest is an area surrounding the nodule;
determining a plurality of characteristics associated with the nodule based on an analysis of the region of interest, wherein the plurality of characteristics is determined using deep learning, and wherein the plurality of characteristics comprises a size of the nodule, a calcification in the nodule, a homogeneity of the nodule and a spiculation of the nodule;
comparing the plurality of characteristics with a trained data model using deep learning, wherein the trained data model comprises historical data related to different sizes of nodules, concentration of calcification in nodules, information associated with homogeneity of nodules, and spiculations for the different nodules;
generating a risk score for the nodule in real time based on the comparison of the plurality of characteristics with the trained data model; and
predicting a lung cancer risk when the risk score for the nodule exceeds a predefined threshold value.

* * * * *